United States Patent [19]

Gall

[11] 4,005,099

[45] Jan. 25, 1977

[54] 1-[(DIMETHYLAMINO)-METHYL]-6-ARYL-4H-IMIDAZO[1,5-A][1,4]BENZODIAZEPINES

[75] Inventor: Martin Gall, Kalamazoo, Mich.

[73] Assignee: The Upjohn Company, Kalamazoo, Mich.

[22] Filed: Nov. 21, 1975

[21] Appl. No.: 634,076

[52] U.S. Cl. .......................... 260/309; 260/296 T; 424/263; 424/273
[51] Int. Cl.² ...................................... C07D 487/04
[58] Field of Search ..................... 260/309, 296 T

[56] References Cited
UNITED STATES PATENTS 3,910,946   10/1975   Gall .................................. 260/309

Primary Examiner—Natalie Trousof
Attorney, Agent, or Firm—Hans L. Berneis

[57] ABSTRACT

Compounds of the formula III

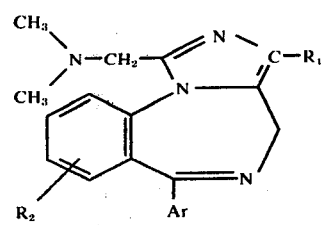

wherein $R_1$ is hydrogen or methyl; wherein $R_2$ is hydrogen, fluoro, chloro, bromo, trifluoromethyl, or nitro; and wherein Ar is phenyl, o-chlorophenyl, o-fluorophenyl, o,o-difluorophenyl, or 2-pyridyl, are produced by a two-step process. The compounds of formula III as well as their pharmacologically acceptable acid addition salts thereof are antidepressant agents possessing additionally antianxiety activity. Thus these compounds III are useful in the treatment of anxieties in mammals and birds, and also as anti-depressants in man.

10 Claims, No Drawings

1-[(DIMETHYLAMINO)-METHYL]-6-ARYL-4H-IMIDAZO[1,5-A][1,4]BENZODIAZEPINES

BACKGROUND OF THE INVENTION

Field of the Invention

This invention is directed to new organic compounds and is particularly concerned with novel 6-phenyl-1-[(dimethylamino)methyl]-4H-imidazo1,5-a][1,4]benzodiazepines and a process for the production thereof.

The novel compounds and the process of production therefore can illustratively represented as follows:

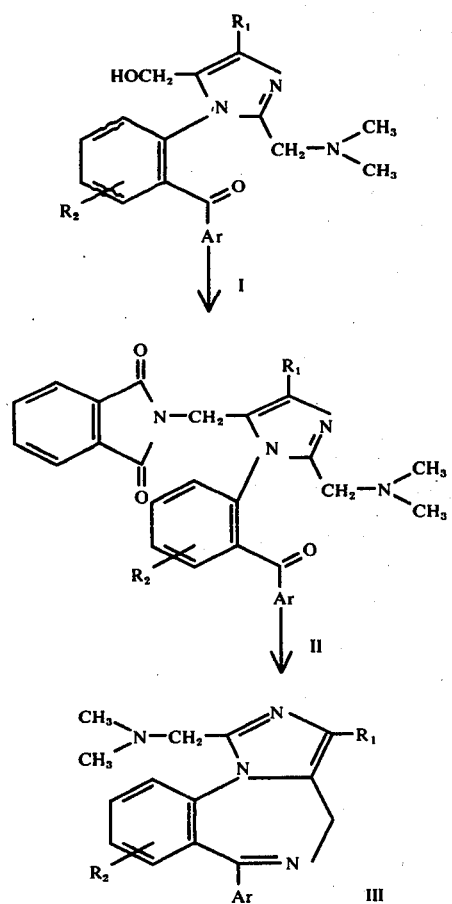

wherein $R_1$ is hydrogen or methyl; wherein $R_2$ is hydrogen, fluoro, chloro, bromo, trifluoromethyl, or nitro, and wherein $A_r$ is phenyl, o-chlorophenyl, o-fluorophenyl, o,o-difluorophenyl, or 2-pyridyl.

The process of this invention comprises: reacting a compound of formula I with phthalimide, triphenylphosphine and thereafter with a dialkyl azodicarboxylic acid to give compound II and reacting compound II with a base e.g. hydrazine hydrate, ethylamine, or an acid to give compound III.

The invention also comprises the production of pharmacologically acceptable acid addition salts of the compounds of formula III above.

If pharmacologically acceptable acid addition salts of III are desired, the selected compound III is reacted with a selected acid either in stoichiometric proportions or with an excess of acid.

DESCRIPTION OF THE PREFERRED EMBODIMENT

The more desirable compounds of this invention have the formula IIIA:

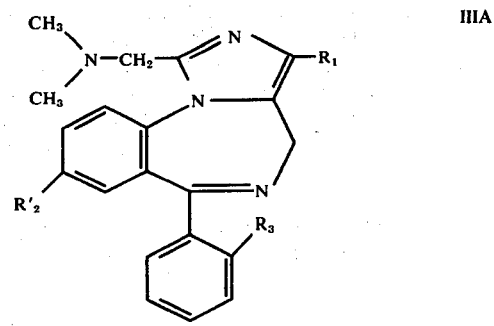

wherein $R_1$ is hydrogen or methyl; wherein $R'_2$ is hydrogen, fluoro, chloro, or trifluoromethyl; wherein $R_3$ is hydrogen, chloro, or fluoro; and the pharmacologically acceptable acid addition salts thereof.

The most desirable compounds of this invention have the formula IIIB:

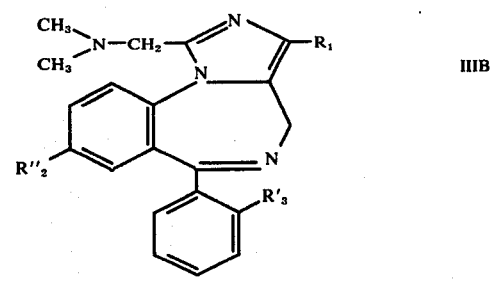

wherein $R_1$ is hydrogen or methyl; wherein $R''_2$ is hydrogen, chloro, or fluoro; and wherein $R'_3$ is hydrogen, or chloro; and the pharmacologically acceptable acid addition salts thereof.

The novel compounds of the formula III including acid addition salts thereof, have sedative, tranquilizing and muscle relaxant effects in mammals including man and birds, and have also antidepressive effects.

The acid addition salts of compounds of formula III contemplated in this invention are hydrochlorides, hydrobromides, hydriodides, sulfates, phosphates, cyclohexanesulfamates, methanesulfonates, and the like, prepared by reacting a compound of formula III with the stoichiometrically calculated amount of the selected pharmacologically acceptable acid.

The anti-anxiety activity of these compounds of formula III was tested by standard tests such as the bicucullin test, γ-butyrolactone potentiation test and the hypoxic stress test.

The anti-depressant activity of compounds of formula III was tested by the antagonism of these compounds to oxotremorine produced hypothermia, potentiation of apomorphine gnawing and yohimbine toxicity. The antidepressant test are shown in detail in U.S. Pat. No. 3,853,881.

The anti-anxiety tests are performed as revealed below:

PROTECTION AGAINST BICUCULLIN-INDUCED T.E. CONVULSIONS

In this procedure, groups of 4 CF-1 (Carnsworth Farms) male mice, weighing 18–22 gm. each, are injected i.p. with the test agent prepared in 0.25% methylcellulose. Thirty minutes later, bicucullin is injected i.v. at 1 mg./kg. Bicuculin (Pierce Chem. Co.) is solubilized in 1N aqueous hydrochloric acid, diluted to a concentration of 1 to 4 mg./ml. with physiological saline and adjusted to a final pH of 5–6 before injection. Mice are observed for 5 minutes after bicucullin injection. A compound is considered to be active if it protects at least 2 of the 4 mice from tonic extensor convulsions during this period. Active compounds are retested using multiple dose levels decreasing at 0.3 or 0.5 log intervals and the number of mice failing to convulse is used as a quantal response to calculate the $ED_{50}$ (Spearman and Karber: Finney, D. J., Statistical Method in Biological Assay, Hafner Publ. Co., N.Y., p. 524, 1952). This procedure is a useful test for detecting compounds with minor tranquilizer or sedative activity.

GAMMA BUTYROLACTONE SLEEP POTENTIATION

Gamma butyrolactone produces loss of righting in mice at doses higher than 400 mg./kg. i.p. At lower doses (200 mg./kg.) the mice do not lose their righting reflex unless previously treated with sub-hypnotic doses of CNS depressant agents. This then provides a technique to study the depressant activity of potential CNS agents.

Groups of 4 male CF-1 mice, weighing 18–22 gm. each, are injected i.p. with the test agent prepared in 0.25% methylcellulose. Thirty minutes later gamma butyrolactone prepared in the same vehicle is injected i.p. at 200 mg./kg. Ten minutes later mice are tested for loss of righting. A compound is considered active if at least 2 of the 4 mice have lost the righting reflex. Active compounds are retested using multiple dose levels decreasing at 0.3 to 0.5 log intervals and the number of mice with loss of righting is used as a quantal response to calculate the $ED_{50}$ (Spearman and Karber: Finney, D. J., Statistical Method in Biological Assay, Hafner Publ. Co., N.Y., p 524, 1952).

PROLONGATION OF HYPOXIC SURVIVAL

Pretreatment of mice exposed to the stress of progressive hypoxia and hypercapnia with anxiolytics results in a prolongation of survival. since tolerance does not appear to develop to the clinial anxiolytic effects of benzodiazepines, the hypoxic survival test is a useful screening technique for anxiolytic drugs.

Male CF-1 derived mice were used in these studies. Thirty minutes after intraperitoneal pretreatment (test agent suspended in 0.25% methylcellulose or vehicle alone, 1 cc./100 gm. body weight) the mice were placed singly in 125 ml. Erlenmeyer flasks. The receptacles were tightly stoppered and the survival time (time from stoppering to the last respiratory effort) of each animal noted. Each compound was tested at three or more doses spaced at 0.3 log intervals. Six mice were used per dose with six vehicle injected controls run simultaneously. The mean (15–18 minutes) and standard deviation (1–2 minutes) of the survival time for the vehicle treated mice were used to convert the data to a quantal form in the following manner. All survival times that differed from the mean of the controls by more than 2 standard deviations were scored as a drug effect. $ED_{50}$'s were calculated by the method of Spearman and Karber (Finney, D. J., Statistical Method in Biological Assay, Hafner Publ. Co., N.Y., 1952).

The compounds of formula IIIB in which $R'_3$ is hydrogen, are particularly active as antidepressants.

The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring, and flavoring agents may be added.

For mammals and birds food premixes, with starch, oatmeal, dried fishmeat, fishmeal, flour, and the like can be prepared.

The compounds of Formula II are further useful to increase meat production in cattle, to provide a more favorable weight versus feed intake ratio.

Compounds of formula III can be used in dosages of 1 mg.-20 mg./kg. in oral or injectable preparations as described above, to alleviate tension and anxiety in mammals, or birds, such as e.g., occurs when animals are in travel. In larger mammals, over 10 kg., lower dosages such as 0.3 to 2.5 mg./kg. are usually adequate.

The starting materials of Formula I of this invention if they are of the benzophenone type or more precisely 2-[2-[(dimethylamino)methyl]-5-hydroxymethylimidazol-1-yl]-benzophenone can be prepared as shown in the preparations 1 through 6 or in U.S. Pat. No. 3,763,179.

The starting material of formula I which has a 2-pyridylcarboxy group is prepared as shown in the preparations 7 through 12.

In carrying out the process of this invention, a compound is reacted with phthalimide and triphenylphosphine in an inert organic solvent at a low temperature, −20° to 10° C. As inert organic solvent tetrahydrofuran, dioxane, dialkylethers e.g. diethyl ether, dibutyl ether can be used. The mixture is then reacted with dialkyl azodicarboxylate in which each alkyl group is of 1 to 3 carbon atoms, inclusive. In the preferred embodiment of this invention starting product and reagents are used in equimolecular ratios. Excess of any one ingredient does not provide any advantage. The reaction mixture is allowed to warm up to room temperature, 20° to 30° C. and stirred for 2 to 48 hours, preferably 10 to 20 hours. The product II is isolated and purified by conventional means such as evaporation of excess solvent, extraction, chromatography and crystallization.

Compound II is cyclized with a reagent producing cyclization in a phthalimido compound of this type. Hydrazine, hydrazine hydrate, mono- or dialkylamines e.g. ethyl- or diethylamine, mono- or dipropylamine, propyl or butylamine, hydrochloric acid, alkali metal bases such as sodium or potassium hydroxide, or sodium or potassium carbonates are useful as cyclization reagents. An inert organic solvent such as a lower alkanol of 1 to 3 carbon atoms, inclusive, is used. Temperatures of 10° to 75° are used, preferably room temperature with stirring of 1 to 48 hours. After the reaction is terminated the product III is obtained and purified by conventional means such as evaporation of the solvent, extraction, chromatography, and crystallization.

The following preparations and examples are illustrative of the processes and products of the present invention, but are not to be construed as limiting.

PREPARATION 1

2-[[2-[(Hydroxymethyl)-1,3-dioxolan-2-yl]-methyl]amino]-7-chloro-5-phenyl-3H-1,4-benzodiazepine A suspension of 7-chloro-1,3-dihydro-5-phenyl-2H-1,4-benzodiazepin-2-thione (34.32 g., 0.12 mol) and 2-(aminomethyl)-2-(hydroxymethyl)-1,3-dioxolane (31 g., 0.24 mole) in 1000 ml. of n-butanol is heated on a steambath overnight under nitrogen. After the butanol is taken off in vacuo, the residue is taken up in cold water and extracted with two 300 ml. portions of chloroform. The chloroform extract is first washed with water, then a saturated salt solution, then dried and reconcentrated in vacuo to a dark red oil. This oil is chromatographed over silica gel to afford 36 g. (78%) of 2-[[2-[(hydroxymethyl)-1,3-dioxolan-2-yl]methyl]amino]-7-chloro-5-phenyl-3H-1,4-benzodiazepine of melting point 165°–168° C. An analytical sample, recrystallized from ethyl acetate, has a melting point of 169°–171° C.

Anal. calcd. for $C_{20}H_{20}ClN_3O_3$ (mw 385.84): C, 62.25; H, 5.22; N, 10.89; Cl, 9.19. Found: C, 62.39; H, 5.41; N, 11.09; Cl, 9.26.

The same reaction is run by treating 50 g. (0.17 mol) of starting compound with 40 g. of the above amino alcohol in one liter of ethanol and heating to reflux for 3 hours to afford 60.4 g. (90%) of 2-[[2-[(hydroxymethyl)-1,3-dioxolan-2-yl]methyl]amino]-7-chloro-5-phenyl-3H-1,4-benzodiazepine, obtained without column chromatography.

PREPARATION 2

8-Chloro-1-(hydroxymethyl)-6-phenyl-4H-imidazo[1,2-a][1,4]benzodiazepine

A solution of 2-[[2-[(hyroxymethyl)-1,3-dioxolan-2-yl[methyl]amino]-7-chloro-5-phenyl-3H-1,4-benzodiazepine (35 g., 0.09 mole) in 75 ml. of concentrated sulfuric acid is stirred under a nitrogen atmosphere, at room temperature, overnight. The above mixture is quenched on ice, neutralized with a 10% aqueous sodium hydroxide solution and extracted with four 200-ml. portions of chloroform. The chloroform extract is first washed with water and then a saturated sodium chloride solution; it is dried over anhydrous sodium sulfate and concentrated in vacuo to afford a brown oil. This is chromatographed over 2 kg. of silica gel by eluting with 3% methanol-chloroform to give 9 g., (32%) of desired 8-chloro-1-(hydroxymethyl)-6-phenyl-4H-imidazolo[1,2-a][1,4]benzodiazepine of melting point 210°–213° C. ($R_f$ 0.37 on silica gel G, 10% methanol-chloroform). An analytical sample is recrystallized from methanolethyl acetate and has a melting point 213°–215° C.

Anal. calcd. for $C_{18}H_{14}ClN_3O$: C, 66.77; H, 4.36; N, 12.98; Cl, 10.95. Found: C, 66.66; H, 4.35; N, 12.96; Cl, 11.00.

PREPARATION 3

5-Chloro-2-[[5-(hydroxymethyl)-2-(dimethylamino)-methyl]-imidazol-1-yl]benzophenone A solution of 8-chloro-1-hyroxymethyl-6-phenyl-4H-imidazolo[1,2-a][1,4]benzodiazepine (6.54 g., 0.02 mole) and formic acid (26.2 g., 0.5 mole) in 13.5 ml. of a 37% aqueous formalin solution is heated at 100° C. for 3 hours under nitrogen. The above mixture is quenched in cold water, neutralized with a 10% aqueous sodium hydroxide solution and extracted with chloroform (thrice, 200 ml.). The chloroform extract is washed with water, a saturated sodium chloride solution, then dried over anhydrous sodium sulfate and concentrated in vacuo to afford a white oil. This is chromatographed over silica gel by eluting with 3% methanol-chloroform mixtures to afford 4 g. of 5-chloro-2-[[5-(hydroxymethyl)-2-(dimethylamino)methyl]imidazol-1-yl]benzophenone (oil). Since brief attempts to crystallize this material failed, the crude oil is used for the next reaction (see Example 1) NMR $CDCl_3$), δ 7.20–8.00 (8H, multiplet, aromatic —CH), δ 6.90 (1H, singlet, imidazolo CH), δ 4.40 (2H, singlet, —NCH$_2$), 4.05 (1H, broad —OH), 3.55 (2H, doublet, —CH$_2$OH), 1.70 (6H, singlet,

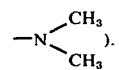
).

PREPARATION 4

2-[[7-Chloro-5-(o-chlorophenyl)-3H-1,4-benzodiazepin-2-yl]amino]propionaldehyde diemthyl acetal A solution of 7-chloro-1,3-dihydro-6-(o-chlorophenyl)-2H-1,4-benzodiazepin-2-thione (6.40 g., 0.020 mol) and α-aminopropionaldehyde dimethyl acetal (6.30 g., 0.060 mol) in 200 ml. of n-butanol is refluxed 20 hours. The solution is cooled to room temperature and the n-butanol is removed in vacuo to give a red-orange oil. The desired product is obtained by trituration from ethyl acetate/hexane. In this way 4.80 g. of 2-[[7-chloro-5-(o-chlorophenyl)-3H-1,4-benzodiazepin-2-yl]amino]propionaldehyde dimethyl acetal of melting point 153°–155° C. is obtained. An analytical sample has a melting point of 155.5°–157° c. (white flowers).

Anal. calcd. for $C_{20}H_{21}Cl_2N_3O_2$: C, 59.12; H, 5.21; H, 10.34; Cl, 17.45. Found: C, 59.15; H, 5.29; N, 10.45; Cl, 17.09.

PREPARATION 5

8-Chloro-2-methyl-6-(o-chlorophenyl)-4H-imidazo[1,2-a][1,4]benzodiazepine

A sample of 2-[[7-chloro-5-(o-chlorophenyl)-3H-1,4-benzodiazepin-2-yl]amino]propionaldehyde dimethyl acetal (2.03 g., 5.00 mmol), dissolved in 60 ml. of monoglyme, is treated with 0.75 ml. (1.30 g., 6.85 mmol) of (reagent-grade) titanium tetrachloride. A vigorous reaction takes place and a brown solid precipitates in the reaction flask. The mixture is refluxed under nitrogen for 4 hours. The reaction mixture is cooled to room temperature, poured into 250 ml. of cold 5% aqueous sodium hydroxide and extracted with chloroform (400 ml.). The chloroform layer is washed with brine, dried over anhydrous magnesium sulfate and concentrated in vacuo to a solid. After crystallization 960 mg. of 8-chloro-2-methyl-6-(o-chlorophenyl)-4H-imidazo[1,2-a][1,4]-benzodiazepine of melting point 169.5°–170.5° C. is obtained.

Anal. calcd. for $C_{18}H_{13}Cl_2N_3$: C, 63.17; H, 3.83; N, 12.28; Cl, 20.72. Found: C, 63.18; H, 3.88; N, 12.35; Cl, 20.75.

PREPARATION 6

2′,5-Dichloro-2-[2-[(dimethylamino)-methyl]-4-methyl 1-yl]benzophenone and
2′,5-dichloro-2-[2-[(dimethylamino)methyl]-4-methyl-5-hydroxymethyl-imidazol-1-yl]benzophenone 8-Chloro-2-methyl-6-(o-chlorophenyl)-4H-imidazo-[1,2-a][1,4]benzodiazepine (3.42 g., 10.0 mmol) is dissolved in 13.1 g. of 88% formic acid. To the resulting solution is added 6.75 ml. of 37% aqueous formaldehyde and the solution is heated to 100°–110° C. for 3 hours, then stirred at room temperature for 3 hours. At this point, a small aliquot is removed and quenched in cold (0°–5° C.) 5% aqueous sodium hydroxide solution, extracted with chloroform, dried over anhydrous magnesium sulfate and analyzed by thin layer chromatography using silica gel G plates and 10% methanol/chloroform as eluent. One major spot of $R_f=0.51$ is present, (Starting material has $R_f=0.63$ in this system) along with a small amount of a slower moving minor component ($R_f=0.28$). The reaction vessel is placed back in the oil bath (set at 100°) and heating is continued overnight for 15 hours. At the end of this period, the entire reaction is quenched in sufficient cold aqueous 5% sodium hydroxide to keep the pH>10 and extraction of the product is made with chloroform. The organic layer is dried over anhydrous magnesium sulfate filtered through Celite and concentrated in vacuo to give an oil, which, by thin layer chromatographic analysis as before, consists almost exclusively of the slow component of $R_f=0.28$. There is no longer evidence of the presence of product of $R_f=0.51$. The oil is crystallized from ethyl acetate to give 2.54 g. (60.7%) of white prisms, melting point 77°–85° C. This solid is recrystallized from ethyl acetate to give 1.77 g. prisms having a melting point 77°–81° C. A small portion is recrystallized from acetone to give colorless needles of melting point 73°–75° C. Analytical data was obtained on the ethyl acetate solvate, $C_{21}H_{21}Cl_2N_3O_2 \cdot \frac{1}{2}C_4H_8O_2$.

Anal. calcd. for $C_{21}H_{21}Cl_2N_3O_2$, mw 418.31: C, 60.29; H, 5.06; N, 10.05; Cl, 16.95. calcd. for $C_{21}H_{21}Cl_2N_3O_2 \cdot \frac{1}{2}CH_3CO_2CH_2CH_3$, mw 462.35: C, 59.74; H, 5.45; N, 9.01; Cl, 15.33. Found: C, 59.53; H, 5.50; N, 8.96; Cl, 15.37.

Melt solvate 10.76% (½mole) EtOAc

In a repeat synthesis, carried out according to preparation 3, unsolvated 2′,5-dichloro-2-[2-[(dimethylamino)methyl]-4-methyl-5-hydroxymethylimidazol-1-yl]-benzophenone is obtained in 55% yield of melting point 164°–166° C.

In the manner given in the previous preparations 1 through 3, other [2-[(dimethylamino)methyl]-5-hydroxymethylimidazol-1-yl]benzophenones can be made such as:

2′,6′,5-trifluoro-2-[2-[(dimethylamino)methyl]-5-hydroxymethylimidazol-1-yl]benzophenone;
5-fluoro-2-[2-[(dimethylamino)methyl]-5-hydroxymethylimidazol-1-yl]benzophenone;
4′,4-dichloro-2-[2-[(dimethylamino)methyl]-5-hydroxymethylimidazol-1-yl]benzophenone;
4,2′-dichloro-2-[2-[(dimethylamino)methyl]-5-hydroxymethylimidazol-1-yl]benzophenone;
6-bromo-2-[2-[(dimethylamino)methyl]-5-hydroxymethylimidazol-1-yl]benzophenone;
2′-fluoro-2-[2-[(dimethylamino)methyl]-5-hydroxymethylimidazol-1-yl]benzophenone;
2′,5-difluoro-2-[2-[(dimethylamino)methyl]-5-hydroxymethylimidazol-1-yl]benzophenone;
5-trifluoromethyl-2-[2-[(dimethylamino)methyl]-5-hydroxymethylimidazol-1-yl]benzophenone;
3-trifluoromethyl-2-[2-[(dimethylamino)methyl]-5-hydroxymethylimidazol-1-yl]benzophenone;
3-trifluoromethyl-2′-fluoro-2-[2-[(dimethylamino)methyl]-5-hydroxymethylimidazol-1-yl]benzophenone;
4-bromo-2′-fluoro-2-[2-[(dimethylamino)methyl]-5-hydroxymethylimidazol-1-yl]benzophenone;
6-bromo-2′-chloro-2-[2-[(dimethylamino)methyl]-5-hydroxymethylimidazol-1-yl[benzophenone; and the like.

In the manner given in preparations 4 through 6, other [2-[(dimethylamino)methyl]-4-methyl-5-hyroxymethylimidazol-1-yl]benzophenones can be made such as:

2′,6′-difluoro-5-chloro-2-[2-[(dimethylamino)methyl]-4-methyl-5-hydroxymethylimidazol-1-yl]benzophenone;
2′,6′,5-trifluoro-2-[2-[(dimethylamino)methyl]-4-methyl-5-hydroxymethylimidazol-1-yl]benzophenone;
2′-chloro-5-fluoro-2-[2-[(dimethylamino)methyl]-4-methyl-5-hydroxymethylimidazol-1-yl]benzophenone;
4′,4-dichloro-2-[2-[(dimethylamino)methyl]-4-methyl-5-hydroxymethylimidazol-1-yl]benzophenone;
2′-chloro-5-nitro-2-[2-[(dimethylamino)methyl]-4-methyl-5-hydroxymethylimidazol-1-yl]benzophenone;
4,2′-dichloro-2-[2-[(dimethylamino)methyl]-4-methyl-5-hydroxymethylimidazol-1-yl]benzophenone;
2′-chloro-5-bromo-2-[2-[(dimethylamino)methyl]-4-methyl-5-hydroxymethylimidazol-1-yl]benzophenone;
2′-fluoro-2-[2-[(dimethylamino)methyl]-4-methyl-5-hydroxymethylimidazol-1-yl]benzophenone;
2′-chloro-2-[2-[(dimethylamino)methyl]-4-methyl-5-hydroxymethylimidazol-1-yl]benzophenone;
2′-chloro-5-trifluoromethyl-2-[2-[(dimethylamino)methyl]-4-methyl-5-hydroxymethylimidazol-1-yl]benzophenone;
3′-chloro-5-fluoro-2-[2-[(dimethylamino)methyl]-4-methyl-5-hydroxymethylimidazol-1-yl]benzophenone;
3-trifluoromethyl-2-[2-[(dimethylamino)methyl]-4-methyl-5-hydroxymethylimidazol-1-yl]benzophenone;
3-trifluoromethyl-2′-fluoro-2-[2-[(dimethylamino)methyl]-4-methyl-5-hydroxymethylimidazol-1-yl]benzophenone;
4′-fluoro-6-chloro-2-[2-[(dimethylamino)methyl]-4-methyl-5-hydroxymethylimidazol-1-yl]benzophenone;
4-bromo-2′-fluoro-2-[2-[(dimethylamino)methyl]-4-methyl-5-hydroxymethylimidazol-1-yl]benzophenone;
5-chloro-2-[2-[(dimethylamino)methyl]-4-methyl-5-hydroxymethylimidazol-1-yl]benzophenone;

6-bromo-2′-chloro-2-[2-[(dimethylamino)methyl]-4-methyl-5-hydroxymethylimidazol-1-yl]benzophenone;

PREPARATION 7

2-[[2-[(Hydroxymethyl)-1,3-dioxolan-2-yl]-methyl]amino]-7-bromo-5-(2-pyridyl)-3H-1,4-benzodiazepine A suspension of 45 mmol of 7-bromo-1,3-dihydro-5-(2-pyridyl)-2H-1,4-benzodiazepine-2-thione and 12 g. (114 mmol) of 2-aminomethyl-2-hydroxymethyl-1,3-dioxolane in 500 ml. of n-butanol is heated to reflux for 4 hours with a stream of nitrogen bubbling through the reaction. (Within 1 hour all solids have dissolved). The solvent is removed in vacuo and the residue taken up in chloroform. The chloroform solution is washed with water and brine, dried over anhydrous sodium sulfate and concentrated to a yellow brown oil in vacuo. On trituration with ethyl acetate this affords 2-[[2-[(hydroxymethyl)-1,3-dioxolan2-yl]methyl]amino]-7-bromo-5-(2-pyridyl)-3H-1,4-benzodiazepine.

PREPARATION 8

8-Bromo-1-hydroxymethyl-6-(2-pyridyl)-4H-imidazo[1,2-a][1,4]benzodiazepine

A solution of 2-[[2-[(hydroxymethyl)-1,3-dioxolan-2-yl]methyl]amino]-7-bromo-5-(2-pyridyl)-3H-1,4-benzodiazepine, in 50 ml. of concentrated sulfuric acid, is allowed to stir, at room temperature, under nitrogen, overnight, poured onto crushed ice and neutralized with an aqueous sodium hydroxide solution. The product is extracted with chloroform and the chloroform washed with brine, dried over sodium sulfate and concentrated to an oil in vacuo. On trituration, 8-bromo-1-hydroxymethyl-6-(2-pyridyl)-4H-imidazo[1,2-a][1,4]benzodiazepine is obtained.

PREPARATION 9

5-Bromo-2-[[5-(hydroxymethyl)-2-[(dimethylamino)-methyl]imidazol-1-yl]phenyl]2-pyridyl ketone A solution of 8-bromo-1-(hydroxymethyl)-6-(2-pyridyl)-4H-imidazo[1,2-a][1,4]benzodiazepine in formic acid is heated to 100° C. for 3 hours with aqueous formaldehyde. The mixture is cooled, neutralized with aqueous sodium hydroxide solution and extracted with chloroform. The extracts are evaporated and the residue twice recrystallized to give 5-bromo-2-[[5-hydroxymethyl-2-[(dimethylamino)methyl]imidazol-1-yl]phenyl]2-pyridyl ketone.

PREPARATION 10

2-[[7-Chloro-5-(2-pyridyl)-3H-1,4-benzodiazepin-2-yl]amino]propionaldehyde dimethyl acetal A solution of 7-chloro-1,3-dihydro-5-(2-pyridyl)-1,4-benzodiazepin-2-thione in butanol solution is refluxed with excess α-aminopropionaldehyde dimethyl acetal. After cooling excess butanol is removed by vacuum distillation and the residue is crystallized from ethyl acetate-hexane to give 2-[[7-chloro-5-(2-pyridyl)-3H-1,4-benzodiazepin-2-yl]amino]propionaldehyde dimethyl acetal.

PREPARATION 11

8-Chloro-2-methyl-6-(2-pyridyl)-4H-imidazo[1,2-a][1,4]benzodiazepine

A solution of 2-[[7-chloro-5-(2-pyridyl)-3H-1,4-benzodiazepin-2-yl]amino]propionaldehyde dimethyl acetal in monoglyme is treated with titanium tetrachloride first at room temperature, then under reflux. The reaction mixure is cooled, neutralized, and extracted with chloroform. The chloroform layer is concentrated in vacuo and the resulting residue crystallized to give 8-chloro-2-methyl-6-(2-pyridyl)-4H-imidazo[1,2-a][1,4]benzodiazepine.

PREPARATION 12

5-Bromo-2-[[2-[(dimethylamino)methyl]-4-methyl-5-(hydroxymethyl)imidazol-1-yl]phenyl]2-pyridyl ketone A solution of 8-bromo-1-(hydroxymethyl)-2-methyl-6-(2-pyridyl)-4H-imidazo[1,2-a][1,4]benzodiazepine in formic acid is heated to 100° C. for 3 hours with aqueous formaldehyde. The mixture is cooled, neutralized with aqueous sodium hydroxide solution and extracted with chloroform. The extracts are evaporated and the residue twice recrystallized to give 5-bromo-2-[[5-(hydroxymethyl)-2-[(dimethylamino)methyl]-4-methylimidazol-1-yl]phenyl]2-pyridyl ketone.

In the manner given in preparations 7 through 9 other 2-[2-[(dimethylamino)methyl-5-(hydroxymethyl)-imidazol-1-yl]phenyl]2-pyridyl ketones can be produced such as:

2′,6′,5-trifluoro-2-[2-[(dimethylamino)methyl]-5-hydroxymethylimidazol-1-yl]phenyl 2-pyridyl ketones;

4′,4-dichloro-2-[2-[(dimethylamino)methyl]-5-hydroxymethylimidazol-1-yl]phenyl 2-pyridyl ketones;

4′,2-dichloro-2-[2-[(dimethylamino)methyl]-5-hydroxymethylimidazo-1-yl]phenyl 2-pyridyl ketones;

6-bromo-2-[2-[(dimethylamino)methyl]-5-hydroxymethylimidazol-1-yl]phenyl 2-pyridyl ketones;

2′-fluoro-2-[2-[(dimethylamino)methyl]-5-hydroxymethylimidazol-1-yl]phenyl 2-pyridyl ketones;

4-trifluoromethyl-2-[2-[(dimethylamino)methyl]-5-hydroxymethylimidazol-1-yl]phenyl 2-pyridyl ketones;

3-trifluoromethyl-2-[2-[(dimethylamino)methyl]-5-hydroxymethylimidazol-1-yl]phenyl 2-pyridyl ketones;

3-trifluoromethyl-2′-fluoro-2-[2-[(dimethylamino)methyl]-5-hydroxymethylimidazo-1-yl]phenyl 2-pyridyl ketones;

4-bromo-2′-fluoro-2-[2-[(dimethylamino)methyl]-5-hydroxymethylimidazol-1-yl]phenyl 2-pyridyl ketones;

6-bromo-2′-chloro-2-[2-[(dimethylamino)methyl]-5-hydroxymethylimidazol-1-yl]phenyl 2-pyridyl ketones; and the like.

In the manner given in preparations 10 through 12, other 2-[2-[(dimethylamino)methyl-4-methyl-5-(hydroxymethyl)imidazol-1-yl]phenyl]2-pyridyl ketones such as:

2′,6′,5-trifluoro-2-[[2-[(dimethylamino)methyl]-4-methyl-5-hydroxymethylimidazol-1-yl]phenyl]2-pyridyl ketone; 4′,4-dichloro-2-[[2-[(dimethylamino)methyl]-4-methyl-5-(hydroxymethyl- )imidazol-1-yl]phenyl]2-pyridyl ketone; 4',2-dichloro-2-[[2-[(dimethylamino)methyl]-4-methyl-5-(hydroxymethyl)imidazol-1-yl]phenyl]2-pyridyl ketone;
6-bromo-2-[[2-[(dimethylamino)methyl]-4-methyl-5-(hydroxymethyl)imidazol-1-yl]phenyl] 2-pyridyl ketone;
2'-fluoro-2-[[2-[(dimethylamino)methyl]-4-methyl-5-(hydroxymethyl)imidazol-1-yl]phenyl]2-pyridyl ketone;
5-trifluoromethyl-2-[[2-[(dimethylamino)methyl]-4-methyl-5-(hydroxymethyl)imidazol-1-yl]phenyl]2-pyridyl ketone;
3-trifluoromethyl-2-[[2-[(dimethylamino)methyl]-4-methyl-5-(hydroxymethyl)imidazol-1-yl]phenyl]2-pyridyl ketone;
3-trifluoromethyl-2'-fluoro-2-[[2-[(dimethylamino)methyl]-4-methyl-5-(hydroxymethyl)imidazol-1-yl]phenyl]2-pyridyl ketone;
4-bromo-2'-fluoro-2-[[2-[(dimethylamino)methyl]-4-methyl-5-(hydroxymethyl)imidazol-1-yl]phenyl]2-pyridyl ketone;
6-bromo-2'-chloro-2-[[2-[(dimethylamino)methyl]-4-methyl-5-(hydroxymethyl)imidazol-1-yl]phenyl]2-pyridyl ketone; and the like.

EXAMPLE 1

5-Chloro-2-[[5-(phthalimidomethyl)-2-(dimethylamino)methyl]imidazol-1-yl]benzophenone A solution of 5-chloro-2-[[5-(hydroxymethyl)-2-(dimethylamino)methyl]imidazol-1-yl]benzophenone (3.77 g., 0.01 mole), triphenylphosphine (2.6 g., 0.01 mole) and phthalimide (1.5 g., 0.01 mole) in 50 ml. of tetrahydrofuran is cooled to 0° C. and treated dropwise with diethyl azodicarboxylate (1.86 g., 0.01 mole). After complete addition, the resulting mixture is stirred at room temperature for 1 hour, then quenched in ice cold water, neutralized with an ice cold 10% aqueous sodium hydroxide solution, and extracted with chloroform (thrice, 200 ml.). The chloroform extract is washed with water, saturated sodium sulfate and concentrated in vacuo to provide an orange oil. This is chromatographed over silica gel by eluting with 3% methanol/97% chloroform mixtures to afford 3.2 g. of a mixture of 5-chloro-2-[[5-(phthalimidomethyl)-2-(dimethylamino)methyl]imidazol-1-yl]benzophenone and reduced diethyl azodicarboxylate. This mixture is used for the reaction in the following Example 2 without any purification.

EXAMPLE 2

8-Chloro-6-phenyl-1-[(dimethylamino)methyl]-4H-imidazo[1,5-a][1,4]benzodiazepine A solution of 5-chloro-2-[[5-(phthalimidomethyl)-2-(dimethylamino)methyl]imidazol-1-yl]benzophenone (3.2 g., 0.006 mole) and hydrazine hydrate (1.2 g., 0.025 mole) in 20 ml. of absolute ethanol is stirred at room temperature, under nitrogen for 18 hours during which time phthalizine is precipitated from the solution. This is filtered and washed with ethanol. The ethanol is taken off in vacuo and the residue is dissolved in chloroform. This is filtered and concentrated in vacuo to afford a yellow oil, which is chromatographed over silica gel by eluting with 3% methanol-97% chloroform mixtures to afford 1.3 g. of 8-chloro-6-phenyl-1-[(dimethylamino)methyl]-4H-imidazo-[1,5-a][1,4]benzodiazepine of melting point 209°–211° C.

An analytical sample, recrystallized from ethyl acetate has a melting point of 213°–215° C.

Anal. calcd. for $C_{20}H_{19}ClN_4$: C, 68.46; H, 5.46; N, 15.97; Cl, 10.10. Found: C, 68.15; H, 5.47; N, 16.22; Cl, 10.38.

EXAMPLE 3

N-[[1-[4-Chloro-2-(o-chlorobenzoyl)phenyl]-2-[(dimethylamino)methyl]-4-methylimidazol-5-yl]methyl]-phthalimide A solution of 8.37 g. (20.0 mmol) of 2',5-dichloro-2-[2-[(dimethylamino)methyl]-4-methyl-5-hydroxymethylimidazol-1-yl]benzophenone, 3.24 g., (22.0 mmol) of phthalimide and 5.76 g., (22.0 mmol) of triphenylphosphine, dissolved in 200 ml. of freshly distilled tetrahydrofuran, is cooled in an ice bath and carefully treated, dropwise and with vigorous stirring, with 3.83 g., (22.0 mmol) of diethyl azodicarboxylate. The addition takes ½ hour and the temperature rises gradually to 25° C. The light orange colored solution is stirred overnight, concentrated, in vacuo and chromatographed over by 800 g. of silica gel be eluting with 3 l. of a 96/4 mixture of chloroform/methanol and 2 l. of a 95/5 mixture of chloroform/methanol. Ten-ml. fractions are collected. Fractions 264–296 are combined to afford 10.3 g. of light green oil which crystallizes from ethyl acetate-hexane mixtures to yield 5.4 g. of fine prisms, of melting point 121°–150° C. An NMR spectrum indicated that the product is contaminated with about ⅓ of an equivalent of $C_2H_5OCO-NH-NH-CO_2-C_2H_5$. Recrystallization from ethyl acetate affords 4.03 g. (36.8%) of N-[[1-[4-chloro-2-(o-chlorobenzoyl)phenyl]-2-[(dimethylamino)methyl]-4-methyl-imidazol-5-yl]methyl-phthalimide of melting point 162°–165° C. A second crop accounts for an additional 0.810 g. (7.4%), melting point 163°–165° C.

Anal. calcd. for $C_{29}H_{24}Cl_2N_4O_3$: C, 63.62; H, 4.42; N, 10.24; Cl, 12.95. Found: C, 63.43; H, 4.48; N, 10.03; Cl, 13.10.

EXAMPLE 4

8-Chloro-6-(o-chlorophenyl)-1-[(dimethylamino)methyl]-3-methyl-4H-imidazo[1,5-a][1,4]benzodiazepine A sample of N-[[1-[4-chloro-2-(o-chlorobenzoyl)phenyl]-2-[(dimethylamino)methyl]-4-methylimidazol-5-yl]-methyl]phthalimide (1.094 g., 2.00 mmol) is suspended in 12 ml. of absolute ethanol, treated with 0.20 ml. (~4.16 mmol) of hydrazine hydrate and heated to 73° C. for 90 minutes. The resulting mixture is filtered and the mother liquors are chromatographed over 80 g. of silica gel by eluting with 90/10 chloroform/methanol mixtures. The product is collected in fractions 28–33 (10 ml. fractions are collected) and is crystallized from ethyl acetate to afford 330 mg. (41.4%) of 8-chloro-6-(o-chlorophenyl)-1-[(dimethylamino)methyl]-3-methyl-4H-imidazo[1,5-a][1,4]-benzodiazepine of melting point 185°–186.5° C.

Anal. calcd. for $C_{21}H_{20}Cl_2N_4$: C, 63.16; H, 5.05; N, 14.03; Cl, 17.75 Found: C, 62.97; H, 5.03; N, 14.29; Cl, 17.67.

EXAMPLE 5

N-[[1-[4-Fluoro-2-(o-chlorobenzoyl)phenyl]-2-[(dimethylamino)methyl]-4-methylimidazol-5-yl]methyl]-phthalimide In the manner given in Example 3, 2'-chloro-5-fluoro-2-[2-[(dimethylamino)methyl]-4-methyl-5-hydroxymethylimidazol-1-yl]benzophenone triphenylphosphine, phthalimide and thereafter diethyl azodicarboxylate are reacted together to give N-[[1-[4-fluoro-2-(o-chlorobenzoyl)-phenyl]-2-[(dimethylamino)methyl]-4-methylimidazol-5-yl]-methyl]phthalimide.

EXAMPLE 6

8-Fluoro-6-(o-chlorophenyl)-1-[(dimethylamino)methyl]-3-methyl-4H-imidazo[1,5-a][1,4]benzodiazepine In the manner given in Example 4, N-[[1-[4-fluoro-2-(o-chlorobenzoyl)phenyl]-2-[(dimethylamino)methyl]-4-methylimidazol-5-yl]methyl]phthalimide in ethanol is heated with hydrazine hydrate to give 8-fluoro-6-(o-chlorophenyl)-1-[(dimethylamino)methyl]-3-methyl-4H-imidazo[1,5-a][1,4]benzodiazepine.

EXAMPLE 7

N-[[1-[4-Nitro-2-(o-chlorobenzoyl)phenyl]-2-[(dimethylamino)methyl]-4-methylimidazol-5-yl]methyl]-phthalimide In the manner given in Example 3, 2'-chloro-5-nitro-2-[2-[(dimethylamino)methyl]-4-methyl-5-hydroxymethylimidazol-1-yl]benzophenone, triphenylphosphine, phthalimide and thereafter diethyl azodicarboxylate are reacted together to give N-[[1-[4-nitro-2-(o-chlorobenzoyl)phenyl]-2-[(dimethylamino)methyl]-4-methylimidazol-5-yl]methyl]-phthalimide.

EXAMPLE 8

8-Nitro-6-(o-chlorophenyl)-1-[(dimethylamino)methyl]-3-methyl-4H-imidazo[1,5-a][1,4]benzodiazepine In the manner given in Example 4, N-[[1-[4-nitro-2-o-chlorobenzoyl)phenyl]-2-[(dimethylamino)methyl]-4-methylimidazol-5-yl]methyl]phthalimide in ethanol is heated with hydrazine hydrate to give 8-nitro-6-(o-chlorophenyl)-1-[(dimethylamino)methyl]-3-methyl-4H-imidazo-[1,5-a][1,4]benzodiazepine.

EXAMPLE 9

N-[[1-[4-Bromo-2-(o-chlorobenzoyl)phenyl]-2-[(dimethylamino)methyl]-4-methylimidazol-5-yl]methyl]-phthalimide In the manner given in Example 3, 2'-chloro-5-bromo-2-[2-[(dimethylamino)methyl]-4-methyl-5-hydroxymethylimidazol-1-yl]benzophenone, triphenylphosphine, phthalimide and thereafter diethyl azodicarboxylate are reacted together to give N-[[1-[4-bromo-2-(o-chlorobenzoyl)phenyl]-2-[(dimethylamino)methyl]-4-methylimidazol-5-yl]methyl]-phthalimide.

EXAMPLE 10

8-Bromo-6-(o-chlorophenyl)-1-[(dimethylamino)methyl]-3-methyl-4H-imidazo[1,5-a][1,4]benzodiazepine In the manner given in Example 4, N-[[1-[4-bromo-2-o-(o-chlorobenzoyl)phenyl]-2-[(dimethylamino)methyl]-3-methylimidazol-5-yl]methyl]phthalimide in n-propanol is heated with hydrazine hydrate to give 8-bromo-6-(o-chlorophenyl)-1-[(dimethylamino)methyl]-3-methyl-4H-imidazo[1,5-a][1,4]benzodiazepine.

EXAMPLE 11

N-[[1-[4-trifluoromethyl-2-(o-chlorobenzoyl)-phenyl]-2-[(dimethylamino)methyl]-4-methylimidazol-5-yl]-methyl]phthalimide In the manner given in Example 3, 2'-chloro-5-trifluoromethyl-2-[2-[(dimethylamino)methyl]-4-methyl-5-hyroxymethylimidazol-1-yl]benzophenone, triphenylphosphine, phthalimide and thereafter diethyl azodicarboxylate are reacted together to give N-[[1-[4-trifluoromethyl-2-(o-chlorobenzoyl)phenyl]-2-[(dimethylamino)methyl]-4-methylimidazol-5-yl]methyl]phthalimide.

EXAMPLE 12

8-Trifluoromethyl-6-(o-chlorophenyl)-1-[(dimethylamino)methyl]-3-methyl-4H-imidazo[1,5-a][1,4]-benzodiazepine In the manner given in Example 4, N-[[1-[4-trifluoromethyl-2-(o-fluorobenzoyl)phenyl]-2-](dimethylamino)methyl]-4-methylimidazo-5-yl]methyl]phthalimide in ethanol is heated with hydrazine hydrate to give 8-trifluoromethyl-6-(o-chlorophenyl)-1-[(dimethylamino)methyl]-3-methyl-4H-imidazo[1,5-a][1,4]benzodiazepine.

EXAMPLE 13

N-[[1-[2-(o-chlorobenzoyl)phenyl]-2-[(dimethylamino)methyl]-4-methylimidazol-5-yl]methyl]phthalimide In the manner given in Example 3, 2'-chloro-2-[2-[(dimethylamino)methyl]-4-methyl-5-hydroxymethylimidazol-1-yl]benzodiazepine, triphenylphosphine, phthalimide and thereafter diethyl azodicarboxylate are reacted together to give N-[[1-[2-(o-chlorobenzoyl)phenyl]-2[(dimethylamino)methyl]-4-methylimidzol-5-yl]methyl]phthalimide.

EXAMPLE 14

6-(o-chlorophenyl)-1-[(dimethylamino)methyl]-3-methyl-4H-imidazo[1,5-a][1,4]benzodiazepine In the manner given in Example 4, N-[[1-[2-(o-chlorobenzoyl)phenyl]-2-[(dimethylamino)methyl]-4-methylimidazol-5-yl]methyl]phthalimide in ethanol is heated with hydrazine hydrate to give 6-(o-chlorophenyl)-1-[(dimethylamino)-methyl]-3-methyl-4H-imidazo[1,5-a][1,4]benzodiazepine.

EXAMPLE 15

N-[[1-[4-Chloro-2-(2,6-difluorobenzoyl)-phenyl]-2-[(dimethylamino)methyl]-4-methylimidazol-5-yl]methyl]phthalimide In the manner given in Example 3, 2',6'-difluoro-5-chloro-2-[2-[(dimethylamino)methyl]-4-methyl-5-hydroxymethylimidazol-1-yl]benzophenone, triphenylphosphine, phthalimide and thereafter diethyl azodicarboxylate are reacted together to give N-[[1-[4-chloro-2-(2,6-difluorobenzoyl)phenyl]-2-[(dimethylamino)methyl]-4-methylimidazol-5-yl]methyl]phthalimide.

EXAMPLE 16

8-chloro-6-(2,6-difluorophenyl)-1-[(dimethylamino)methyl]-3-methyl-4H-imidazo[1,5-a][1,4]benzodiazepine In the manner given in Example 4, N-[[1-[4-chloro-2-(2,6-difluorobenzoyl)phenyl]-2-[(dimethylamino)methyl]-4-methylimidazol-5-yl]methyl]phthalimide in methanol is refluxed with hydrazine hydrate to give 8-chloro-6-(2,6-difluorophenyl)-1-[(dimethylamino)methyl]-3-methyl-4H-imidazo[1,5-a][1,4]benzodiazepine.

EXAMPLE 17

N-[[1-[4-Fluoro-2-(o-fluorobenzoyl)phenyl]-2-[(dimethylamino)methyl]imidazol-5-yl]methyl]phthalimide In the manner given in Example 3, 2',5-difluoro-2-[2-[(dimethylamino)methyl]-5-hydroxymethylimidazol-1-yl]-benzophenone, triphenylphosphine, phthalimide and thereafter diethyl azodicarboxylate are reacted together to give N-[[1-[4-fluoro-2-(o-fluorobenzoyl)-phenyl]-2-[(dimethylamino)methyl]imidazol-5-yl]methyl]phthalimide.

EXAMPLE 18

8-Fluoro-6-(o-fluorophenyl)-1-[(dimethylamino)methyl]-4H-imidazo[1,5-a][1,4]benzodiazepine In the manner given in Example 4, N-[[1-[4-fluoro-2-(o-fluorobenzoyl)phenyl]-2-[(dimethylamino)methyl]-imidazol-5-yl]methyl]phthalimide in ethanol is heated with hydrazine hydrate to give 8-fluoro-6-(o-fluorophenyl)-1-[(dimethylamino)methyl]-4H-imidazo[1,5-a][1,4]benzodiazepine.

EXAMPLE 19

N-[[1-[4-Bromo-2-(2-pyridylcarbonyl)phenyl]-2-[(dimethylamino)methyl]imidazol-5-yl]methyl]phthalimide In the manner given in Example 3, 5-bromo-2-[2-[(dimethylamino)methyl]-5-(hydroxymethyl)imidazol-1-yl]-phenyl-2-pyridyl ketone, triphenylphosphine phthalimide and thereafter diethyl azodicarboxylate are reacted together to give N-[[1-[4-bromo-2-(pyridylcarbonyl)-phenyl]-2-[(dimethylamino)methyl]imidazol-5-yl]methyl]phthalimide.

EXAMPLE 20

8-Bromo-6-(2-pyridyl)-1-[(dimethylamino)-methyl]-4H-imidazo[1,5-a][1,4]benzodiazepine In the manner given in Example 4, N-[[1-[4-bromo2-(2-pyridylcarbonyl)phenyl]-2-[(dimethylamino)methyl]-imidazol-5-yl]methyl]phthalimide in ethanol is heated with hydrazine hydrate to give 8-bromo-6-(2-pyridyl)-1-[(dimethylamino)methyl]-4H-imidazo[1,5-a][1,4]benzodiazepine.

EXAMPLE 21

N-[[1-[4-Chloro-2-(2-pyridylcarbonyl)phenyl]-2-[(dimethylamino)methyl]-4-methylimidazol-5-yl]methyl]-phthalimide In the manner given in Example 3, 5-chloro-2-[2-[(dimethylamino)methyl]-4-methyl-5-(hydroxymethyl)imidazol-1-yl]phenyl-2-pyridyl ketone, triphenylphosphine, phthalimide and thereafter diethyl azodicarboxylate are reacted together to give N-[[1-[4-chloro-2-(2-pyridylcarbonyl)phenyl]-2-[(dimethylamino)methyl]-4-methylimidazol-5-yl]methyl]phthalimide.

EXAMPLE 22

8-Chloro-6-(2-pyridyl)-1-[(dimethylamino)-methyl]-3-methyl-4H-imidazo[1,5-a][1,4]benzodiazepine In the manner given in Example 4, N-[[1-[4-chloro2-(2-pyridylcarbonyl)phenyl]-2-[(dimethylamino)methyl]-4-methylimidazol-5-yl]methyl]phthalimide in ethanol is heated with hydrazine hydrate to give 8-chloro-6-(2-pyridyl)-1-[(dimethylamino)methyl]-3-methyl-4H-imidazo[1,5-a][1,4]benzodiazepine.

EXAMPLE 23

N-[[1-[4-Trifluoromethyl-2-(2-pyridylcarbonyl)-phenyl]-2-[(dimethylamino)methyl]-4-methylimidazol-5-yl]-methyl]phthalimide In the manner given in Example 3, 5-trifluoromethyl-2-[2-[(dimethylamino)methyl]-4-methyl-5-hydroxymethylimidazol-1-yl]phenyl-2-pyridyl ketone, triphenylphosphine, phthalimide and thereafter diethyl azodicarboxylate are reacted together to give N-[[1-[4-trifluoromethyl-2-(2-pyridylcarbonyl)phenyl]-2-[(dimethylamino)methyl]-4-methylimidazol-5-yl]methyl]phthalimide.

EXAMPLE 24

8-Trifluoromethyl-6-(2-pyridyl)-1-[(dimethyl-amino)-methyl]-3-methyl-4H-imidazo[1,5-a][1,4]benzodiazepine In the manner given in Example 4, N-[[1-[4-trifluoromethyl-2-(2-pyridylcarbonyl)phenyl]-2-[(dimethylamino)-methyl]-4-methylimidazol-5-yl]methyl]phthalimide in ethanol is heated with hydrazine hydrate to give 8-trifluoromethyl-6-(2-pyridyl)-1-[(dimethylamino)methyl]-3-methyl-4H-imidazo[1,5-a][1,4]benzodiazepine.

EXAMPLE 25

N-[[1-[4-Fluoro-2-(m-chlorobenzoyl)phenyl]-2-[(dimethylamino)methyl]-4-methylimidazol-5-yl]methyl]-phthalimide In the manner given in Example 3, 3'-chloro-5-fluoro-2-[2-[(dimethylamino)methyl]-4-methyl-5-hydroxymethylimidazol-1-yl]benzophenone, triphenylphosphine, phthalimide and thereafter diethyl azodicarboxylate are reacted together to give N-[[1-[4-fluoro-2-(m-chlorobenzoyl)phenyl]-2-[(dimethylamino)methyl]-4-methylimidazol-5-yl]methyl]phthalimide.

EXAMPLE 26

8-Fluoro-6-(m-chloropnenyl)-1-[(dimethylamino)methyl]-3-methyl-4H-imidazo[1,5-a][1,4]benzodiazepine In the manner given in Example 4, N-[[1-[4-fluoro-2-(m-chlorobenzoyl)phenyl]-2-[(dimethylamino)methyl]-4-methylimidazol-5-yl]methyl]phthalimide in ethanol is heated with hydrazine hydrate to give 8-fluoro-6-(m-chlorophenyl)-1-[(dimethylamino)methyl]-3-methyl-4H-imidazo[1,5-a][1,4]benzodiazepine.

EXAMPLE 27

N-[[1-[3-chloro-2-(p-fluorobenzoyl)phenyl]-2-[(dimethylamino)methyl]-4-methylimidazol-5-yl]methyl]-phthalimide In the manner given in Example 3, 4'-fluoro-6-chloro-2-[2-[(dimethylamino)methyl]-4-methyl-5-hydroxymethylimidazol-1-yl]benzophenone, triphenylphosphine, phthalimide and thereafter diethyl azodicarboxylate are reacted together to give N-[[1-[3-chloro-2-(4-fluorobenzoyl)phenyl]-2-[(dimethylamino)methyl]-4-methylimidazol-5-yl]methyl]phthalimide.

EXAMPLE 28

7-Chloro-6-(p-fluorophenyl)-1-[(dimethylamino)methyl]-3-methyl-4H-imidazo[1,5-a][1,4]benzodiazepine In the manner given in Example 4, N-[[1[3-chloro-2-(p-fluorobenzoyl)phenyl]-2-[(dimethylamino)methyl]-4-methylimidazol-5-yl]methyl]phthalimide in ethanol is heated with hydrazine hydrate to give 7-chloro-6-(p-fluorophenyl)-1-[(dimethylamino)methyl]-3-methyl-4H-imidazo[1,5-a][1,4]benzodiazepine.

EXAMPLE 29

N-[[1-[4-Chloro-2-(benzoyl)phenyl]-2-[(dimethylamino)methyl]-4-methylimidazol-5-yl]methyl]-phthalimide In the manner given in Example 3, 5-chloro-2-[2-[(dimethylamino)methyl]-4-methyl-5-hydroxymethylimidazol-yl]benzophenone, triphenylphosphine, phthalimide and thereafter diethyl azodicarboxylate are reacted together to give N-[[1-[4-chloro-2-(benzoyl)phenyl]-2-[(dimethylamino)methyl]-4-methylimidazol-5-yl]methyl]phthalimide.

EXAMPLE 30

8-Chloro-6-phenyl-1-[(dimethylamino)methyl]-3-methyl-4H-imidazo[1,5-a][1,4]benzodiazepine In the manner given in Example 4, N-[[1-[4-chloro2-benzoylphenyl]-1-[(dimethylamino)methyl]-4-methylimidazol-5-yl]methyl]phthalimide in ethanol is heated with hydrazine hydrate to give 8-chloro-6-phenyl-1-[dimethylamino)methyl]-3-methyl-4H-imidazo[1,5-a][1,4]benzodiazepine.

EXAMPLE 31

N-[[1-[4-Fluoro-2-(benzoylphenyl)]-2-[(dimethylamino)methyl]imidazol-5-yl]methyl]phthalimide In the manner given in Example 3, 5-fluoro-2-[2-(dimethylamino)methyl]-5-hydroxymethylimidazol-1-yl]-benzophenone, triphenylphosphine, phthalimide and thereafter diethyl azodicarboxylate are reacted together to give N-[[1-[4-fluoro-2-(benzoylphenyl)]-2-[(dimethylamino)-methyl]imidazol-5-yl]methyl]phthalimide.

EXAMPLE 32

8-Fluoro-6-phenyl-1-[(dimethylamino)methyl]-4H-imidazo[1,5-a][1,4]benzodiazepine In the manner given in Example 4, N-[[1-[4-fluoro-2-(benzoylphenyl)]-2-[(dimethylamino)methyl-]imidazol-5-yl]methyl]phthalimide in ethanol is heated with hydrazine hydrate to give 8-fluoro-6-phenyl-1-[(dimethylamino)-methyl]-4H-imidazo[1,5-a][1,4]benzodiazepine.

EXAMPLE 33

N-[[1-[4-trifluoromethyl-2-(benzoylphenyl)]-2-[(dimethylamino)methyl]-4-methylimidazol-5-yl]methyl]-phthalimide In the manner given in Example 3, 2'-chloro-5-trifluoromethyl-2-[2-[(dimethylamino)methyl]-4-methyl-5-hydroxymethylimidazol-1-yl]benzophenone; triphenylphosphine, phthalimide and thereafter diethyl azodicarboxylate are reacted together to give N-[[1-[4-trifluoromethyl-2-(benzoylphenyl)]-2-[(dimethylamino)methyl]-4-methylimidazol-5-yl]methyl]phthalimide.

EXAMPLE 34

8-Trifluoromethyl-6-phenyl-1-[(dimethylamino)methyl]-3-methyl-4H-imidazo[1,5-a][1,4]benzodiazepine In the manner given in Example 4, N-[[1-[4-trifluoromethyl-2-(benzoylphenyl)]-2-[(dimethylamino)-methyl]-4-methylimidazol-5-yl]methyl]phthalimide in ethanol is heated with hydrazine hydrate to give 8-trifluoromethyl-6-phenyl-1-[(dimethylamino)methyl]-3-methyl-4H-imidazo[1,5-a][1,4]benzodiazepine.

Treatment of the compounds of formula III with a pharmacologically acceptable acid such as hydrochloric, hydrobromic, phosphoric, sulfuric, acetic, propionic, toluenesulfonic, methanesulfonic, tartaric, citric, lactic, malic, maleic, or cyclohexanesulfamic acids produces the pharmacologically acceptable salts of these compounds of formula III. The salts can be used for the same purposes as the free base compounds of formula III.

Salt formation is achieved in conventional manner by reacting the compound of formula III with an excess or one equivalent of a selected acid in a suitable medium e.g. water, alkanol, ether, or acetone and recovering the salt by evaporating the solvent, preferably in vacuo.

I claim:

1. A compound of the formula III:

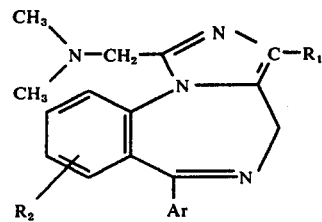

wherein $R_1$ is hydrogen or methyl; wherein $R_2$ is hydrogen, fluoro, chloro, bromo, trifluoromethyl, or nitro; and wherein $A_r$ is phenyl, o-chlorophenyl, o-fluorophenyl, o,o-difluorophenyl, or 2-pyridyl, and the pharmacologically acceptable acid addition salts thereof.

2. A compound according to claim 1, of the formula IIIA:

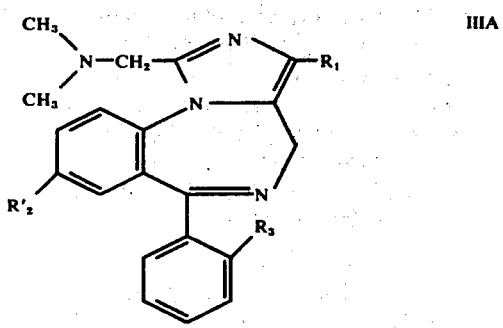

wherein $R_1$ is hydrogen or methyl; wherein $R'_2$ is hydrogen, fluoro, chloro, or trifluoromethyl; wherein $R_3$ is hydrogen, chloro, or fluoro, and the pharmacologically acceptable acid addition salts thereof.

3. A compound according to claim 1, of the formula IIIB:

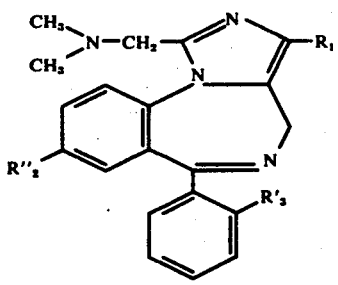

wherein $R_1$ is hydrogen or methyl; wherein $R''_2$ is hydrogen, chloro, or fluoro; and wherein $R'_3$ is hydrogen or chloro and the pharmacologically acceptable acid addition salts thereof.

4. A compound according to claim 1, wherein $A_r$ is 2-pyridyl, $R_1$ is hydrogen, $R_2$ is 8-bromo, and the compound is therefore 8-bromo-1-[(dimethylamino)methyl]-6-(2-pyridyl)-4H-imidazo[1,5-a][1,4]benzodiazepine.

5. A compound according to claim 3, wherein $R_1$ is $CH_3$, $R''_2$ is 8-chloro, $R'_3$ is o-chloro and the compound is therefore 8-chloro-1-[(dimethylamino)methyl]-6-(o-chlorophenyl)-3-methyl-4H-imidazo[1,5-a][1,4]benzodiazepine.

6. A compound according to claim 3, wherein $R_1$ and $R'_3$ are hydrogen, $R''_2$ is 8-chloro, and the compound is therefore 8-chloro-1-[(dimethylamino)methyl]-6-phenyl4H-imidazo[1,5-a][1,4]benzodiazepine.

7. A compound according to claim 3, wherein $R_1$ is methyl, $R''_2$ is 8-chloro, $R'_3$ is hydrogen, and the compound is therefore 8-chloro-1-[(dimethylamino)methyl]-3-methyl-6-phenyl-4H-imidazo[1,5-a][1,4]benzodiazepine.

8. A compound according to claim 3, wherein $R_1$ and $R'_3$ are hydrogen, $R''_2$ is o-fluoro and the compound is therefore 8-fluoro-1-[(dimethylamino)methyl]-6-phenyl-4Himidazo[1,5-a][1,4]benzodiazepine.

9. A compound according to claim 3, wherein $R_1$ is methyl; $R''_2$ is 8-trifluoromethyl, $R'_3$ is hydrogen, and the compound is therefore 8-trifluoromethyl-1-[(dimethylamino)methyl]-3-methyl-6-phenyl-4H-imidazo[1,5-a][1,4]benzodiazepine.

10. A compound according to claim 3, wherein $R_1$ is hydrogen, $R''_2$ is 8-fluoro, $R'_3$ is o-fluoro; and the compound is therefore 8-fluoro-1-[(dimethylamino)methyl]-6-(o-fluorophenyl)-4H-imidazo[1,5-a][1,4]benzodiazepine.

* * * * *